United States Patent [19]
Lehan et al.

[11] Patent Number: 5,699,164
[45] Date of Patent: Dec. 16, 1997

[54] TELECENTRIC REFLECTION HEAD FOR OPTICAL MONITOR

[75] Inventors: John P. Lehan, Benicia; Charles K. Carniglia, Antioch, both of Calif.

[73] Assignee: The BOC Group, Inc., Murray Hill, N.J.

[21] Appl. No.: 627,435

[22] Filed: Apr. 4, 1996

[51] Int. Cl.⁶ .................................................. G01N 21/55
[52] U.S. Cl. ............................................................ 356/445
[58] Field of Search ........................... 356/445, 446; 359/663

[56] References Cited

U.S. PATENT DOCUMENTS

| | | | |
|---|---|---|---|
| 4,199,219 | 4/1980 | Suzki et al. | 356/445 |
| 4,398,787 | 8/1983 | Balasubramanian . | |
| 4,560,862 | 12/1985 | Eastman et al. . | |
| 4,740,708 | 4/1988 | Batchelder . | |
| 5,055,663 | 10/1991 | Morimoto et al. . | |
| 5,252,836 | 10/1993 | Matthews et al. | 356/445 |

OTHER PUBLICATIONS

James, J.F. and R.S. Sternberg; *The Design of Optical Spectrometers;* Chapman and Hall Ltd.; 1969; pp. 167–182. (no month available).

Eastman, Jay M.; "Optical Thin Films"; *Contemporary Optics;* The Institute of Optics, Rochester, New York; 1986; pp. 5.10–5.12. (no month available).

Macleod, H.A.; *Thin–Film Optical Filters*, Second Edition; Macmillan Publishing Company; 1986; pp. 423–432. (no month available).

"Instruction Manual for the Model 191 Series Specular Gonioreflectometer Head"; EG&G Gamma Scientific, San Diego, California; Jun. 15, 1992; p.28.

*Primary Examiner*—Frank G. Font
*Assistant Examiner*—Amanda Merlino
*Attorney, Agent, or Firm*—David A. Draegert; Salvatore P. Pace

[57] ABSTRACT

The use of a telecentric system allows for minimizing the changes in the measured radiometric quantity as a result of defocus or tilt of the object under measurement or of the detector. In a preferred embodiment, a telecentric illuminating system is provided, which illuminates an object from a source. A telecentric receiving system receives reflections from the object and relays them to a detector. In another preferred embodiment, a telecentric system is also described that is appropriate for radiance or radiant intensity measurements.

17 Claims, 13 Drawing Sheets

E = stop
FX = front focal point of lens X
FX' = rear focal point of lens X
E' = image of stop (virtual stop)
Chief ray heights multiplied by five.

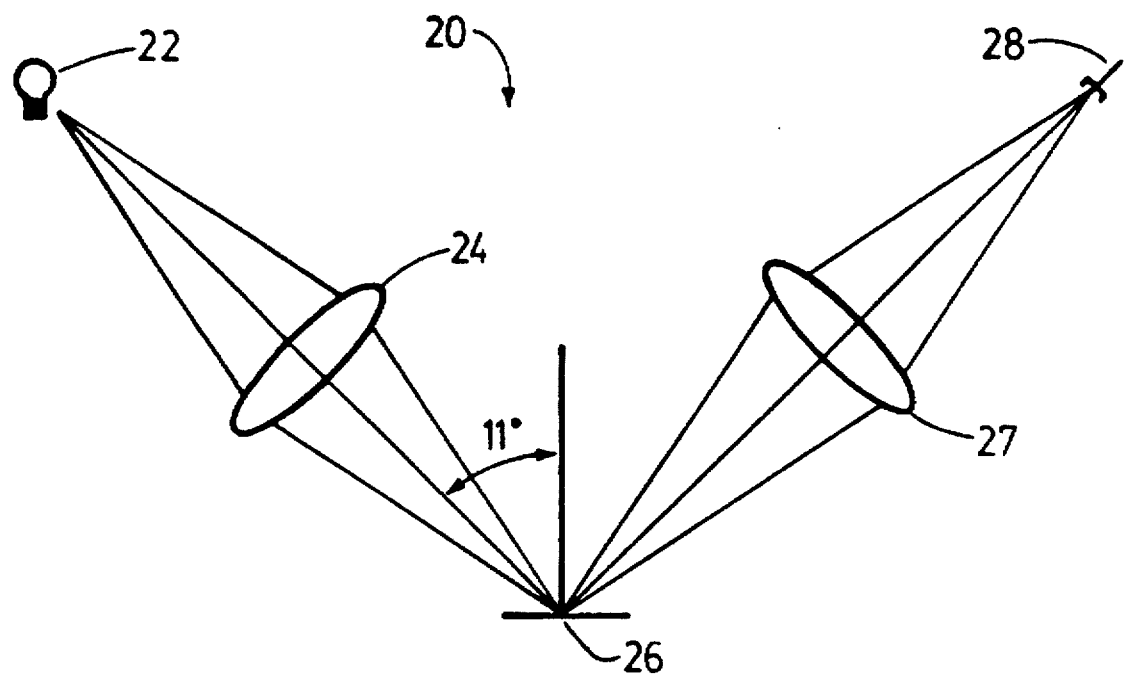
FIG._1.
(PRIOR ART)
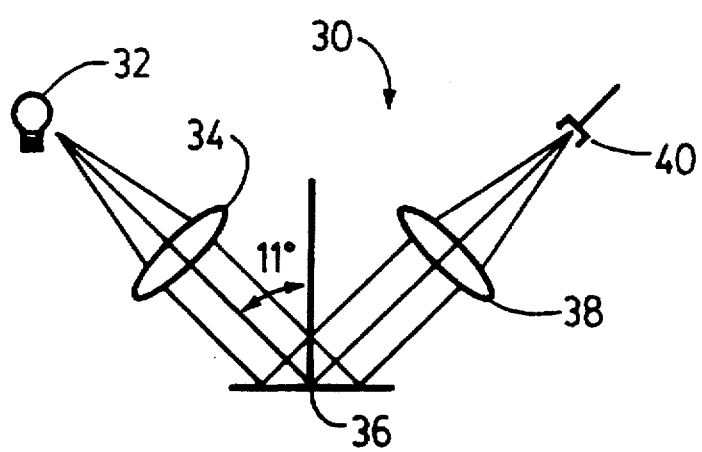
FIG._2.
(PRIOR ART)

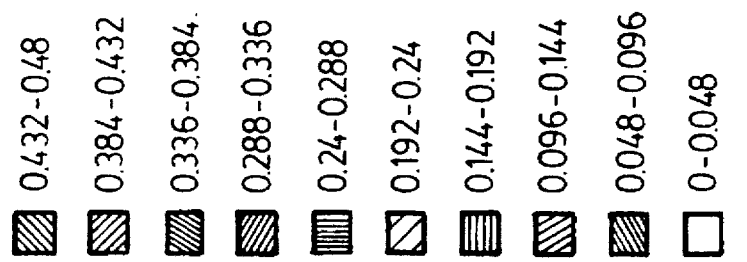
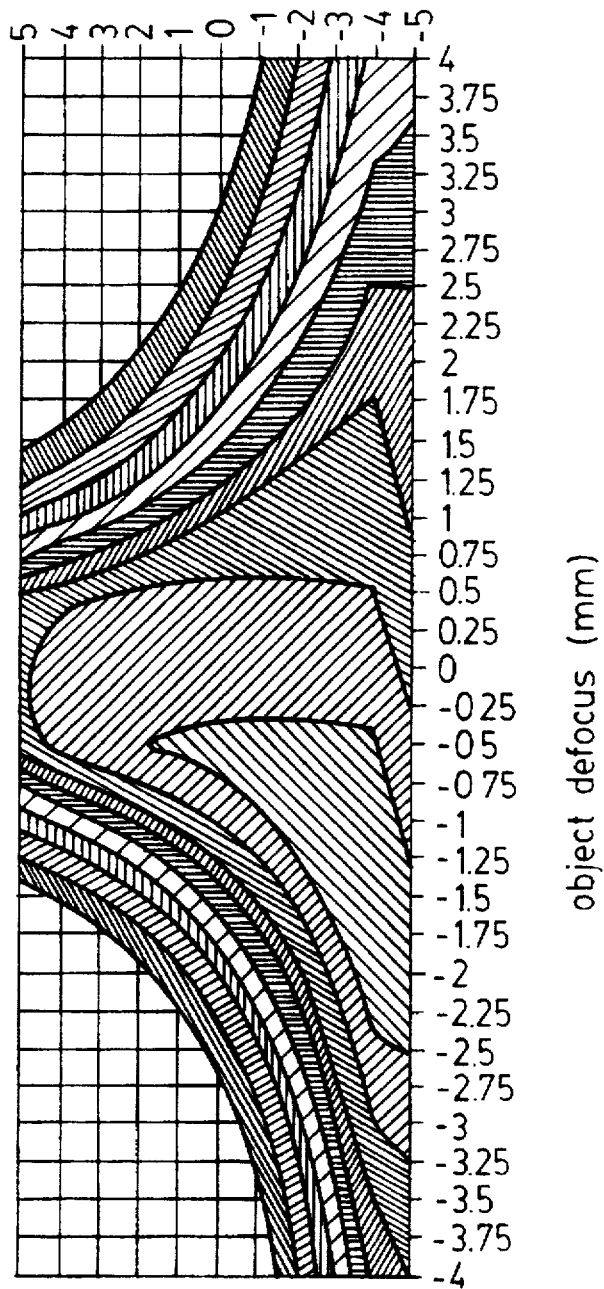
FIG._3.
(Background)

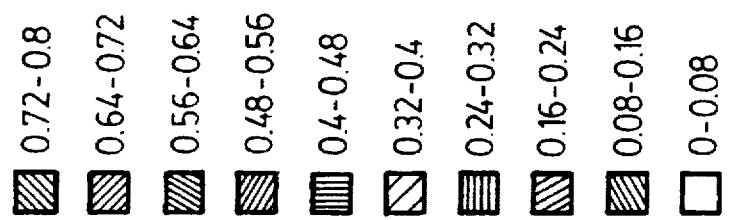
object tilt in plane of incidence (degrees)
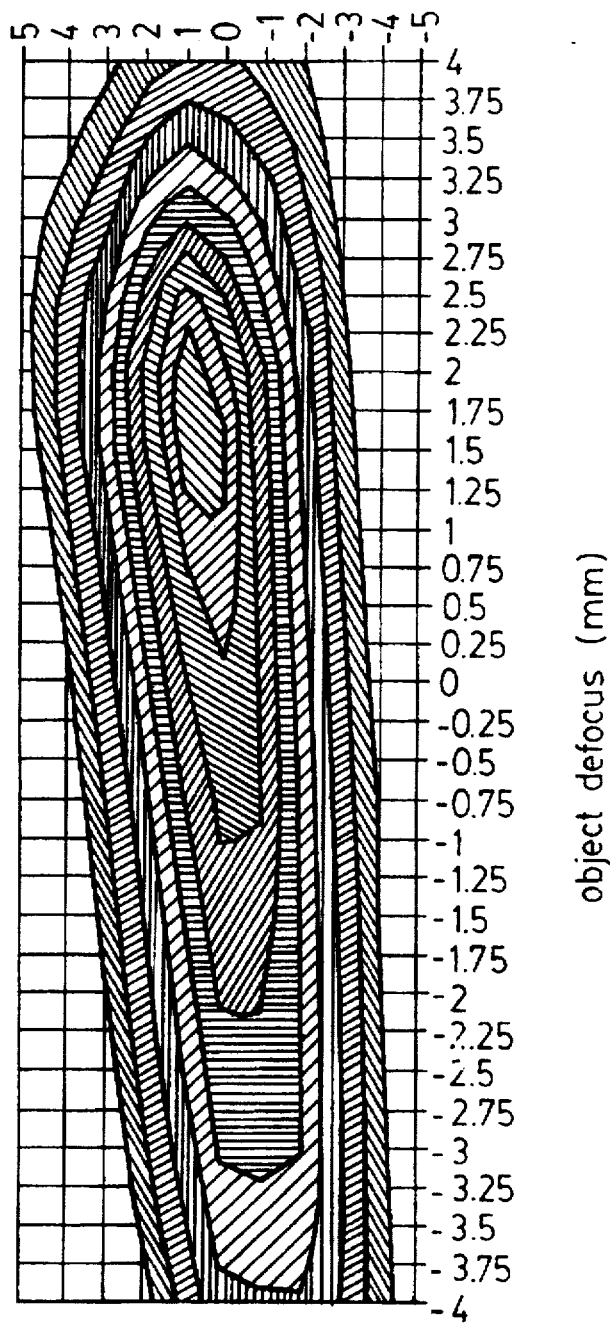
object defocus (mm)
FIG._4. (Background)

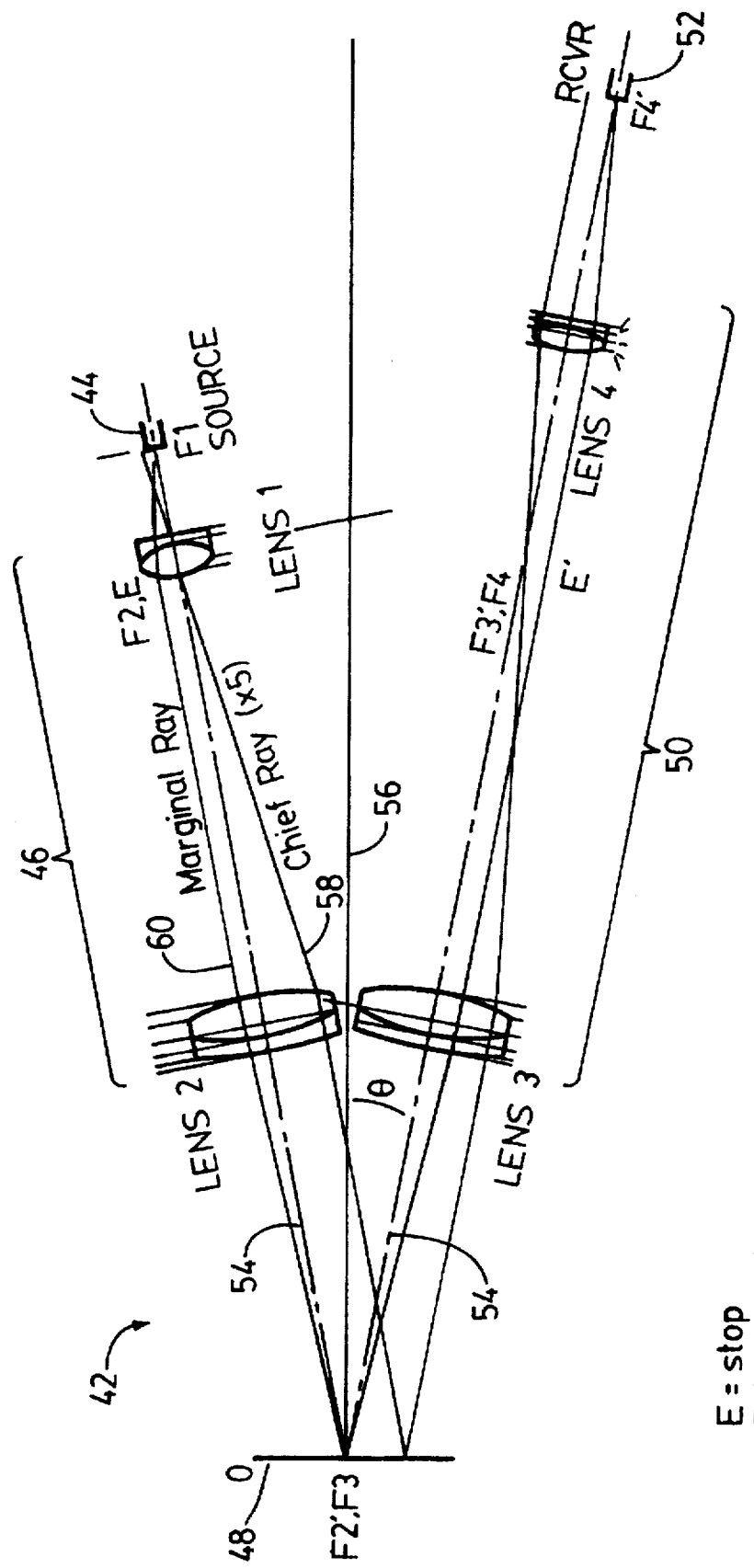
FIG._5.

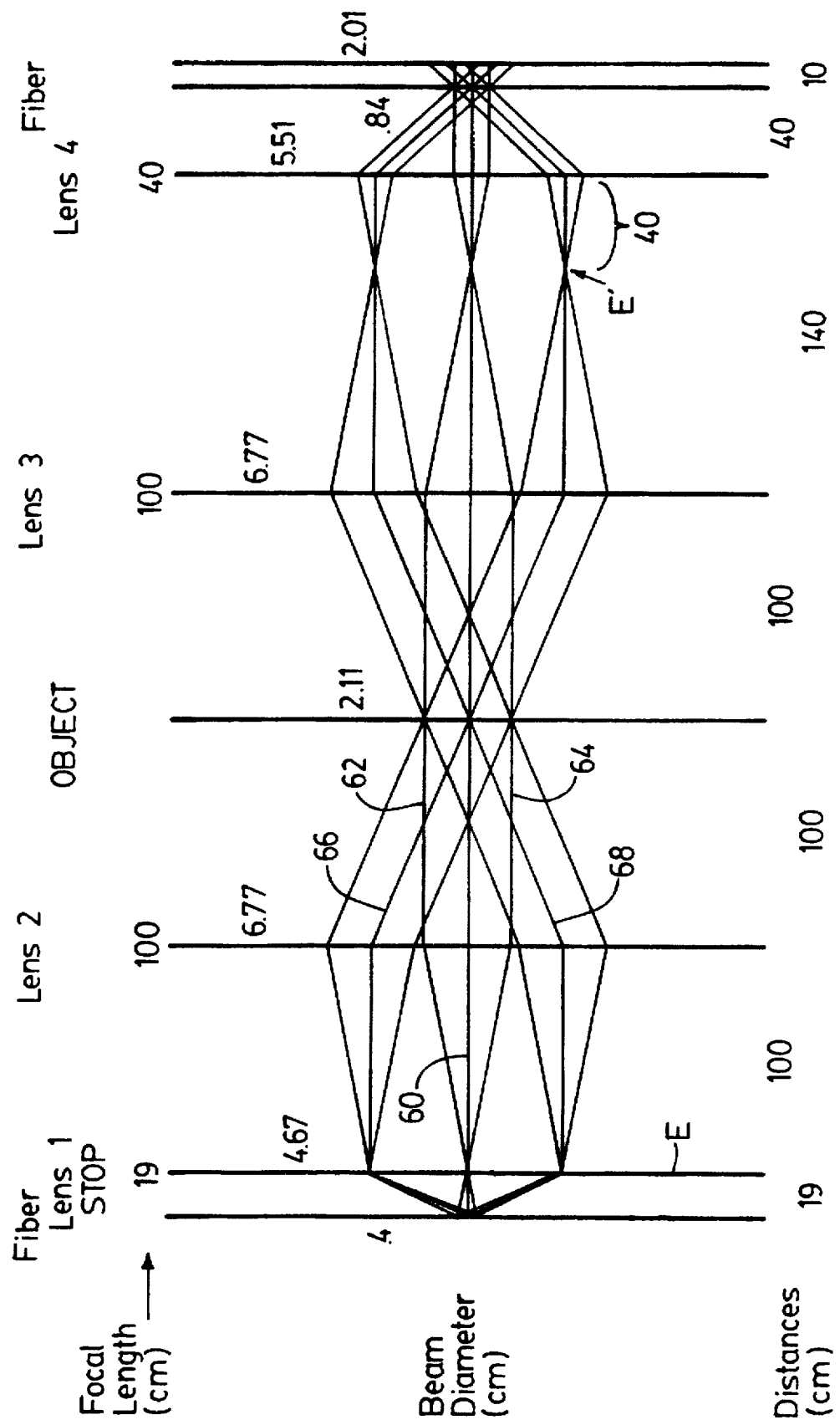
FIG._6.

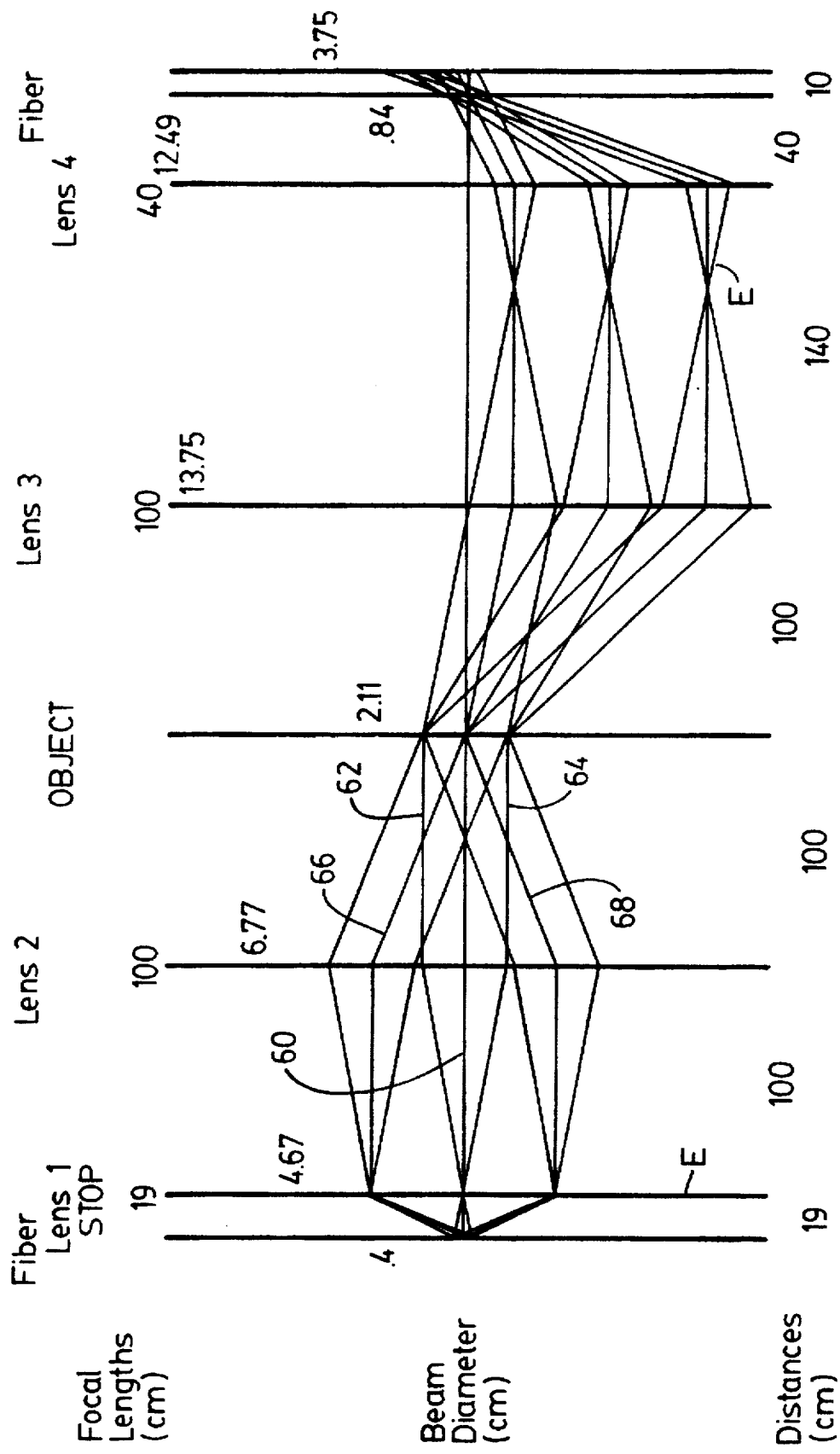
FIG._7.

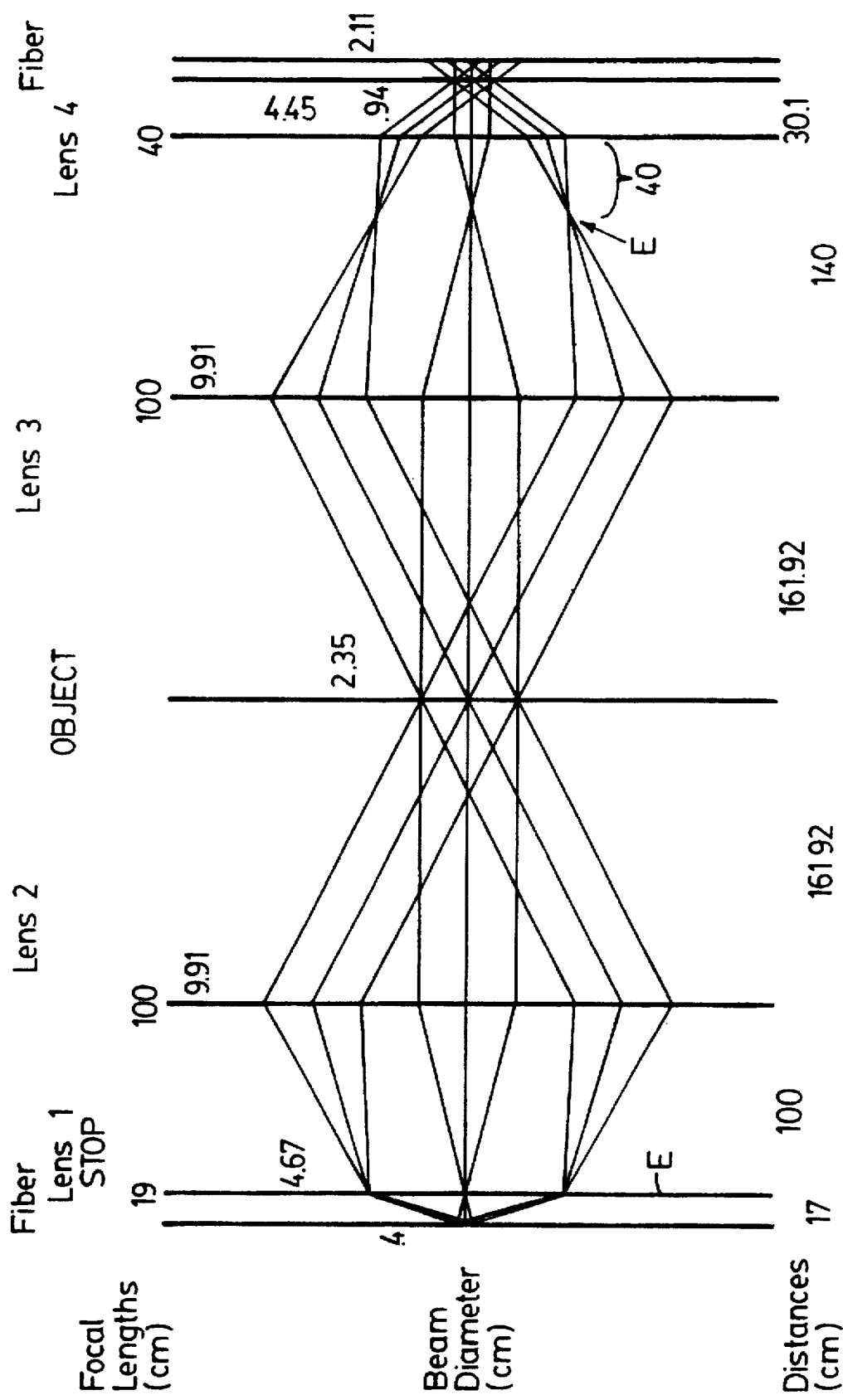
FIG._8.

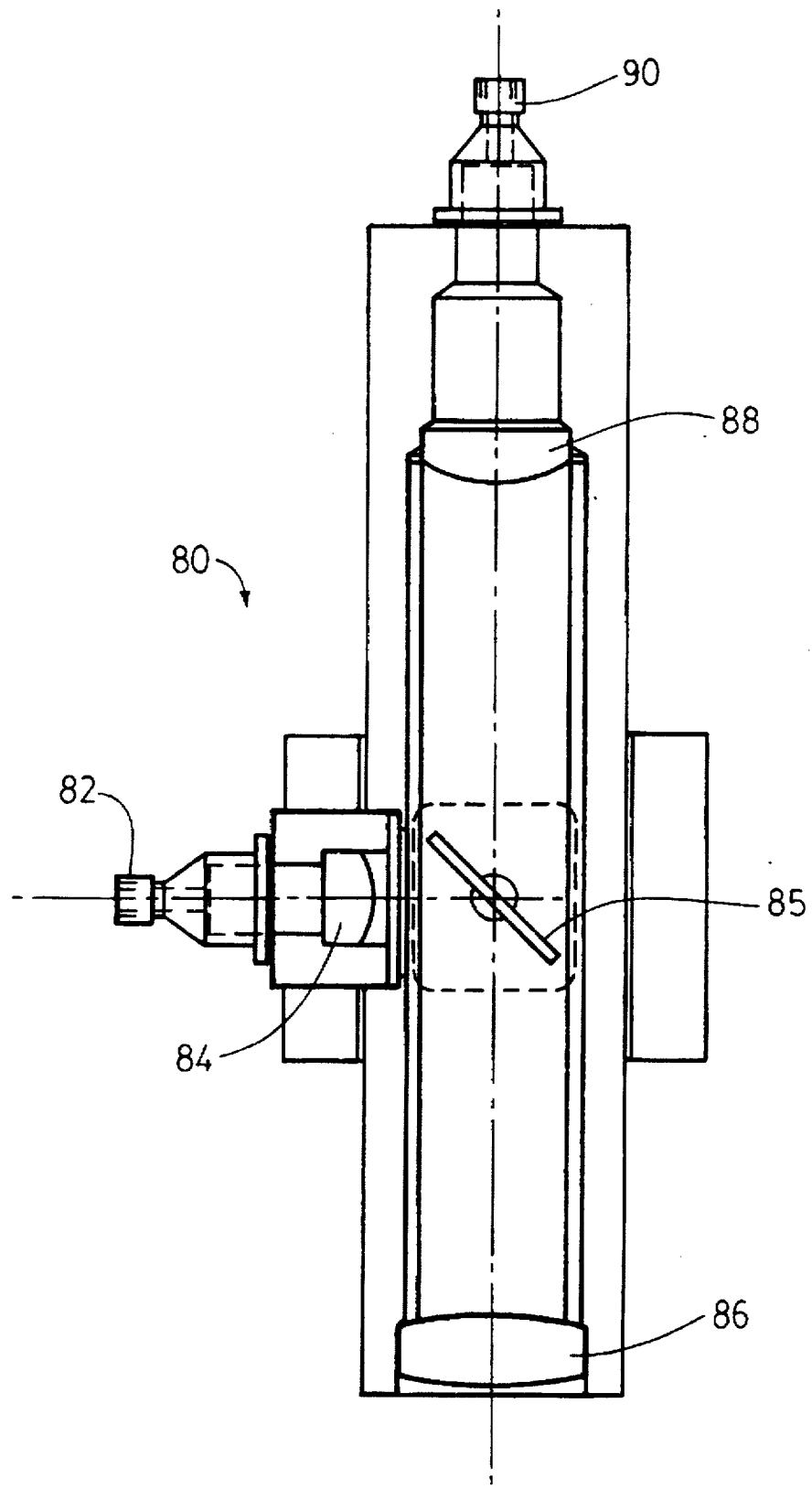
FIG._9.

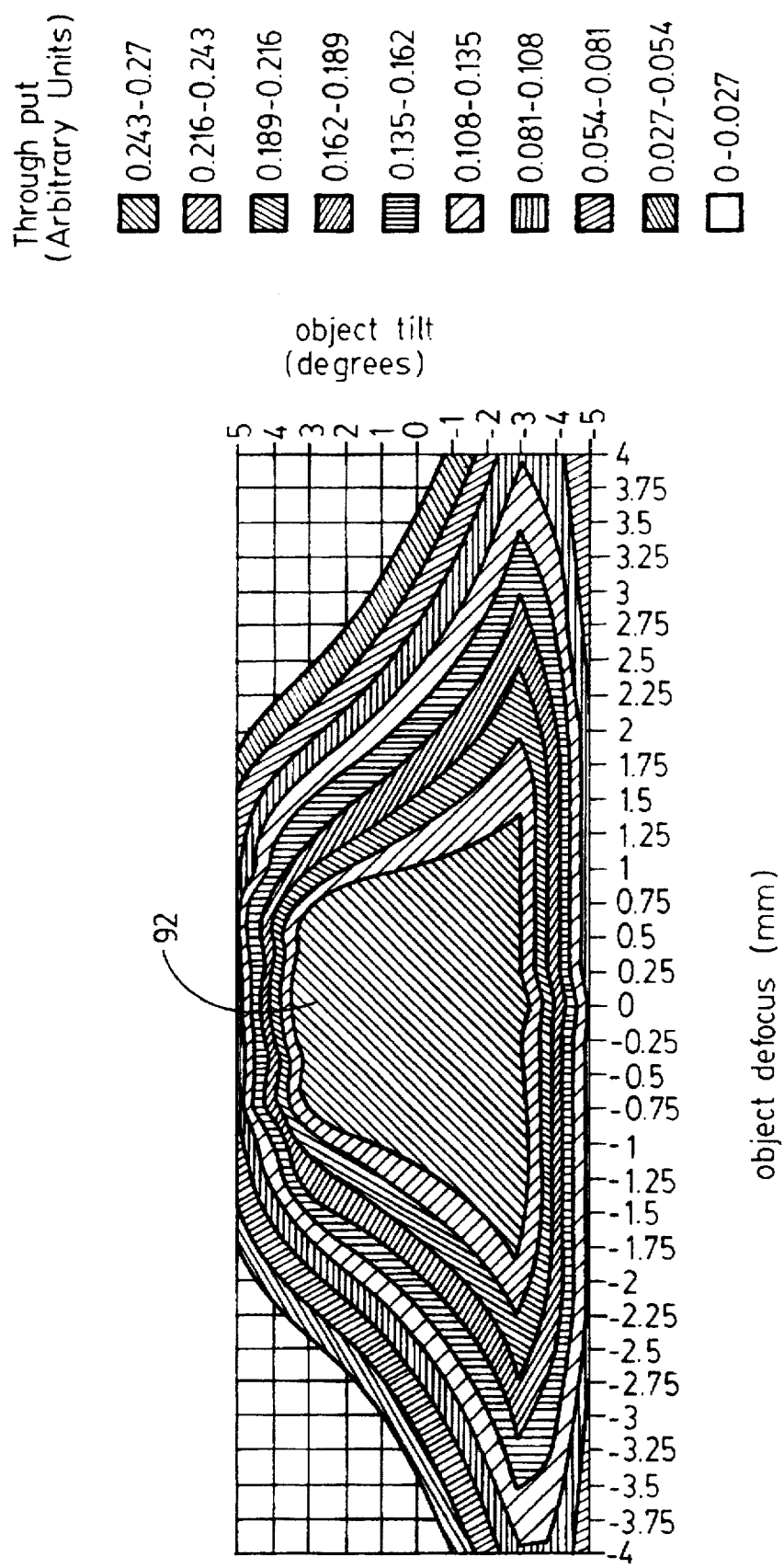
FIG._10.

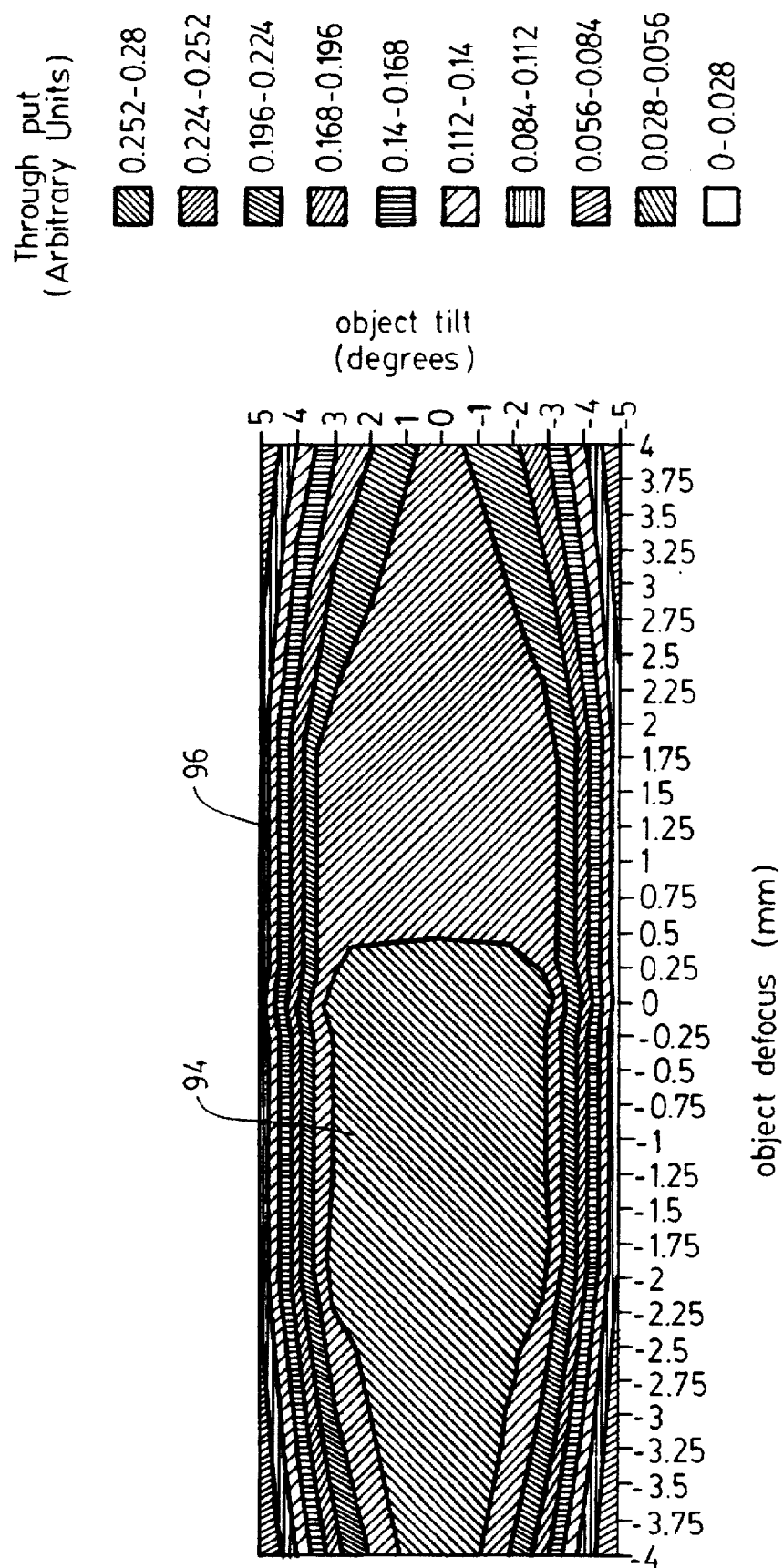
FIG._11.

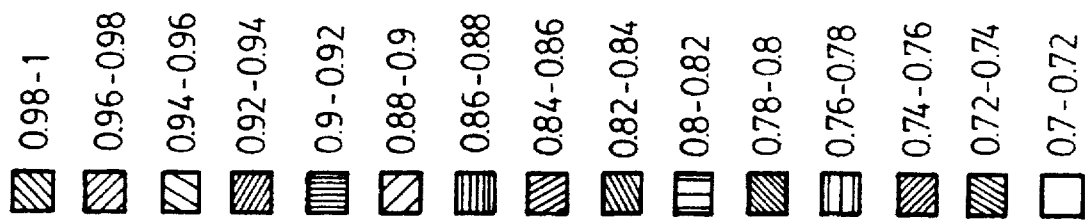
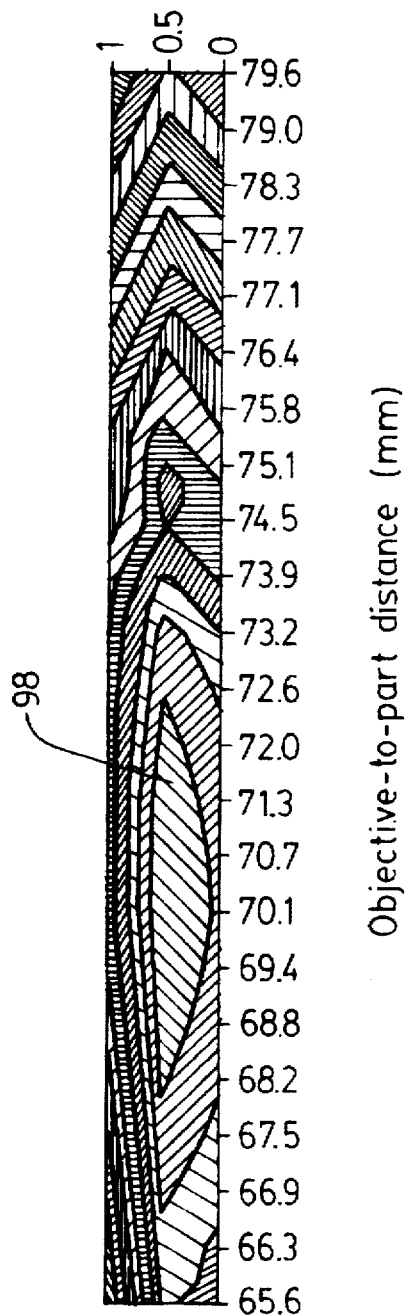
FIG._12.

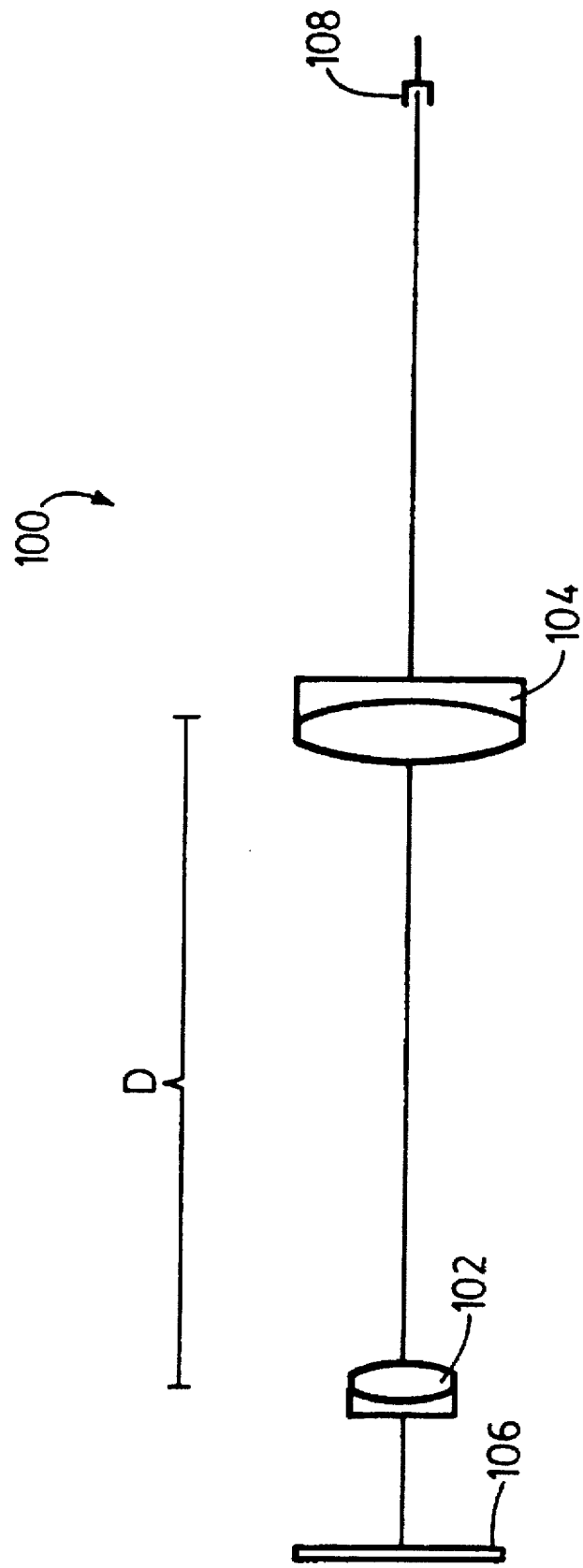
FIG._13.

TELECENTRIC REFLECTION HEAD FOR OPTICAL MONITOR

BACKGROUND OF THE INVENTION

The present invention relates to optical measurement systems. More particularly, the present invention relates to systems for measuring the reflectance of an object.

In reflectance measurements, errors can occur due to any tilt or defocus of the object. On a production line, control of the tilt or position of the object under test is problematic, especially if making contact to the part may damage it or make it unusable for subsequent production steps. It is desired to have a reflectance measurement system, in which variations in position or tilt of the object relative to the test apparatus do not cause significant variations in the measured reflectance.

A typical reflectivity measurement system consists of an optical system to illuminate the sample being measured and an optical system to collect the reflected light. Here an optical system refers to a collection of lenses and apertures. The illumination and collection optical systems may be completely distinct, or they may share some or all of their lenses and apertures. The illumination system relays the light from a light source to the sample. The collection system relays the light reflected from the sample to the detector. To produce an accurate and reproducible reflectivity measurement, it is necessary that the illumination system relay a constant fraction of the light from the source to the sample and that the collection system relay a constant fraction of the reflected light from the sample to the detector. Two key factors which affect the fraction of the light relayed by the systems are the tilt and the position of the sample being measured. These factors have the strongest effect on the reflected light relayed by the collection system. For example, if the angle or tilt of the part changes, the position of the light at the detector plane might change, causing the light to miss the detector, either partially or completely. Similarly, a change in position of the sample would affect the size of the beam illuminating the detector, and thus the intensity of the light at the detector plane.

The tilt and position variations of the sample can occur for several reasons: The sample holder might not be rigid or the sample might not sit in the same position in the sample holder from measurement to measurement. The sample could be moving past the reflectivity measuring device and not be kinematically connected to it. The sample could be curved so that the distance and angle of the sample might depend on its lateral location relative to the reflectivity monitor. An example of a measurement configuration which could involve variability of position and angle occurs in the in-line sputter deposition of glass panels. The panels are not rigidly supported as they are moved passed the reflectivity measuring device and the glass can flex, causing defocus and tilt. If the pieces being coated are CRTs which have curved surfaces, the defocus and tilt problems are amplified because the position and angle of the surface being measured change as the CRT moves past the reflectivity measurement device.

SUMMARY OF THE INVENTION

The measurement system of the present invention uses a telecentric optical system to minimize the dependence of the radiometric measurement on the position of the object being measured.

Telecentric optical systems are generally used with microscopes in order that an out-of-focus object will appear to be the same size as an in-focus object to aid in size measurements. For example, the highest point of a curved meniscus will appear to be at the same height when viewed through a telecentric optical system in spite of slight variations in its distance from the optical system. Scanners sometimes also use telecentric systems. In scanner systems, the optical path of the light between the object being scanned and the image varies due to inaccurate positioning of the object or image plane. The telecentric scanning system compensates for the path-length error. An example of a telecentric scanning system is Batchelder U.S. Pat. No. 4,740,708.

In common applications of telecentric optical systems, it is metric accuracy of the object which is of interest; namely, that features of the object appear to have the same size regardless of a slight defocus of the object itself.

In the case of a reflectivity measurement, a sample is illuminated by a spot of light and the intensity of the reflected light is measured. There are no specific dimensions or features of the sample that need to be measured, and so it is not obvious what the advantages of a telecentric optical system would be in such a case.

The measurement system of the present invention uses telecentric optics to minimize the position and tilt dependence of a radiometric rather than a metric characteristic of an object. In one reflectivity measurement embodiment of the present invention, a telecentric illuminating system is used to receive light from an extended source and relay it to the object. In this case, the telecentric system includes a lens or group of lenses with the stop located at the front focal plane of the lens or group of lenses. This insures that the size of the image of the source formed on the object is independent of the position of the object relative to the lens system. A telecentric collection system is used to relay the light reflected by the object onto a detector. The image of the stop of the illumination system is located at the front focal point of a lens or group of lenses in the collection system so that the size of the image formed at the detector is independent of its exact location relative to the optical system.

A feature of this invention is that the detector is smaller than the image formed by the collection system so that the detector is overfilled. Because the detector is overfilled, it is not obvious why the lateral dimension or size of the image is important. However, the size of the image determines the irradiance of the image, since the irradiance of the image is the optical power contained in the image divided by its area, which in turn is related to the size of the image. Thus, the advantage of the telecentric systems is that the irradiance of the final image is independent of the exact position of the object being measured, and so the amount of light collected by the detector is not dependent on the exact position of the object being measured.

In a preferred embodiment, the stop is sized so that it passes only light within the angles for which the radiance of the source is approximately uniform. This maintains a uniform irradiance at the detector position.

In a preferred embodiment, the source and detector comprise optical fibers. Optical fibers can provide an approximately uniform radiance over some range of angles.

In one embodiment, the optical axis through the telecentric illuminating system and the optical axis through the telecentric receiving system are tilted with respect to one another. It is desired that this angle be as small as practical to reduce the effects of tilt or defocus of the object on system performance. In a preferred embodiment, this angle is the smallest angle with which the physical entities can still be spatially separated.

An alternate embodiment uses a beam splitter so that the light can be incident normal to the object surface. In this embodiment, the light from the source passes through the stop, reflects from a beam splitter and is relayed to the object to be measured. The light will reflect from the object and then be relayed back to the beamsplitter. A portion of this light passes through the beamsplitter and is relayed to the detector. A disadvantage of this embodiment is that a large percentage of the light from the source never reaches the detector. This reduces the efficiency of the device.

The present invention can be used in systems in which the object may change in position, a few percentage points of the focal lengths of the system, or may tilt a few degrees. The system can also be used with systems in which the detector is difficult to position accurately.

A telecentric optic system placed between an object and a detector can also be used for radiance measurements. In radiance measurements, the tilt and/or poor positioning of the object produce similar problems to those discussed above with respect to the reflectance measurements.

BRIEF DESCRIPTION OF THE DRAWINGS

The above and other features and aspects of the present invention will become more apparent upon the reading of the following detailed description in conjunction with the accompanying drawings, in which:

FIG. 1 is a diagram of a reflectance measurement system employing a simple focal relay system.

FIG. 2 is a diagram of a reflectance measurement system employing an afocal relay system with pseudo-collimated light incident upon the object.

FIG. 3 is a computer simulation of the throughput performance of the focal system of FIG. 1 where the included half-angle between the axes of rotation of the two lenses is 11 degrees. The contours show the dependence of the throughput on the tilt and position of the object.

FIG. 4 is a computer simulation of throughput performance of an afocal collimating system where the included half-angle between axes of rotation of the two lenses is again 11 degrees. The contours show the dependence of the throughput on the tilt and position of the object.

FIG. 5 is a diagram of a reflectance measurement system, including a telecentric illuminating system and a telecentric receiving system.

FIG. 6 is a diagram showing selective illustrative rays passing through a thin lens equivalent telecentric system. (In FIGS. 6, 7, and 8, the diagram of the optical system has been unfolded at the plane of the object so that the illuminating and collection optical systems can be seen more clearly.)

FIG. 7 is a diagram showing selective illustrative rays passing through a thin lens equivalent telecentric system with a 1 degree tilt of the object.

FIG. 8 is a diagram illustrating a telecentric system, in which the lenses are not operating at infinite conjugates.

FIG. 9 is a cross-sectional drawing of a telecentric reflectance measurement system with a beam splitter positioned so that the illuminating light is normally incident on the object.

FIG. 10 is a computer simulation showing the throughput for a telecentric optical system similar to that of FIG. 5.

FIG. 11 is a computer simulation showing the throughput of the telecentric optical system similar to the one shown in FIG. 9 where the illuminating light is normally incident on the object.

FIG. 12 is a graph of experimental data for a prototype of the telecentric system shown in FIG. 9 illustrating the measured throughput.

FIG. 13 is a diagram of an alternate embodiment of a telecentric system of the present invention for radiance measurements.

DEFINITIONS

Figure 14:
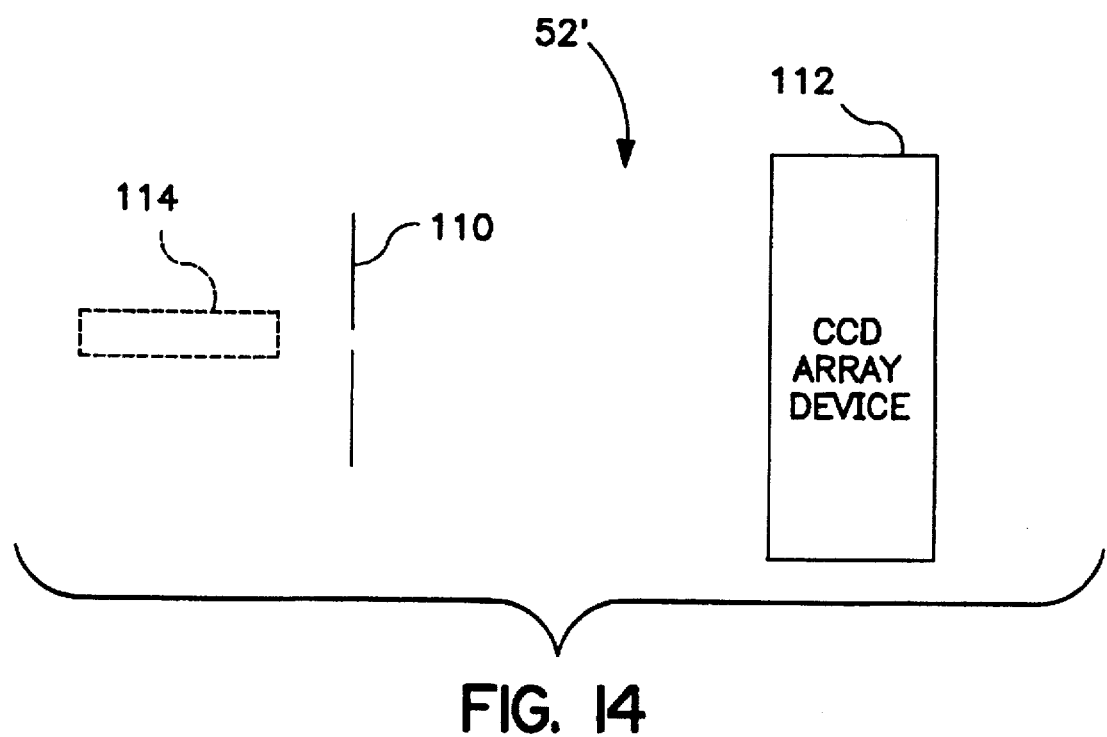
FIG. 14 is a diagram of a complex detector using a spectrograph and a CCD array.
Figure 15:
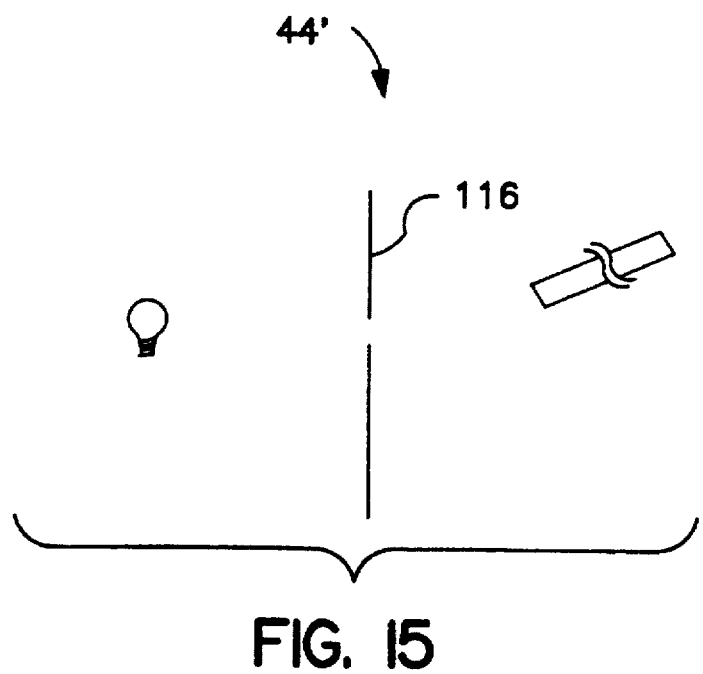
FIG. 15 is a complex source using a spectrograph.

Source: The source is any physical thing that emits light. In the discussion below this also applies to an optical system not detailed here that conducts light to the optical system in question. For example, an optical fiber conducting light from a remote light bulb would be called a source for the purposes of this discussion.

Object: The object is any physical thing that reflects or emits light so that some light coming from it enters the optical system of interest.

Image: An image is a refocusing of the light waves emanating from an object that are combined to the same distribution of irradiance as from the original object to within a scaling factor (in the absence of aberrations). In this invention, the system will be described as "imaging" a source on an object and the detector even though the image planes can be slightly off from these positions as a result of deviations of the object or detector from the optimal position or tilt.

Optical axis: In rotationally-symmetric optical systems an imaginary line through the centers of rotation of all the optical elements.

Magnification: This is the ratio of the image dimension to object dimension. The magnification can be greater than, equal to, or less than unity.

Ray: This is an imaginary construction of the normal to a wavefront. It is used to trace the effect of lenses, etc., on the wavefronts as the waves pass through the optical system if the effects of diffraction are ignored.

Stop: This is an aperture that limits the extent of the cone of rays able to pass through the system.

Pupil: This is the image of the stop formed by the lenses. Also called a virtual stop.

Chief ray: This is a special ray that begins at the edge of the object and passes through the center of the system stop. Its height at an image plane defines the image size.

Marginal ray: The marginal ray is the companion construct to the chief ray. The marginal ray begins at the center of the object (on the optical axis) and passes through the edge of the stop. The marginal ray crossing the optical axis locates an image plane.

Conjugates: These are object-image pairs. These are optically equivalent entities within a scale factor (the magnification).

Infinite conjugates: This is a particular object-image pair where one of the pair is at the focal point of the lens and the other is at infinity.

Collimated light: A special condition where all light rays are parallel (usually to the optical axis). This is created by placing a point source at the focal point of a lens.

Pseudo-collimated light: This is a special condition where the marginal rays are parallel (usually to the optical axis). This is created by placing an (usually small) extended source at the focal point of a lens.

Telecentricity: Telecentricity describes a special relation of the chief rays in a system. A system is telecentric on the object side if the chief rays in the object space are parallel to the optical axis. Equivalently, the entrance pupil is at infinity. A system is telecentric on the image side if the chief rays in the image space are parallel to the optical axis. Equivalently, the exit pupil is at infinity. In the present invention we will use the term telecentric to refer to optical systems which are telecentric on the image side.

Note that several of the preferred embodiments of this invention involve two telecentric optical systems, but this does not imply a doubly telecentric system. A doubly telecentric system is a single telecentric system which is telecentric on both the object side and the image side.

Additionally, a discussion of optical terms is given in MIL-STD-1241A: Optical Terms and Definitions.

DETAILED DESCRIPTION OF THE PREFERRED EMBODIMENT

FIGS. 1 and 2 show other possible solutions to a reflectance measurement system than the system of the present invention. These possible solutions are given as examples to highlight the advantages of the present invention discussed below. FIG. 1 shows a focal measurement system 20. Light from a source 22 is focused by the lens 24 onto an object 26. The light reflects from the object through lens 27, which refocuses the light onto a detector 28. A disadvantage of the system of FIG. 1 is that it is very sensitive to the position of the object 26. If the object 26 moves, the irradiance at the detector 28 will change. This change in irradiance will cause errors in the reflectance measurement.

FIG. 3 shows a computer simulation of the dependence of the throughput on the tilt and position of the object for a focal system with an 11 degree incident angle. Note that the system is tilt insensitive, as shown by the contours which extend along the y-axis. The system is, however, sensitive to changes in position of the object as shown by the contours which extend along the x-axis.

FIG. 2 is a diagram of an afocal collimating system 30 again with an 11 degree incident angle. Light from source 32 is pseudo-collimated by lens 34. The light reflects off the object 36 and the reflection is focused by the lens 38 onto a detector 40. This system is better than the focal system above for changes in position of the object 36, but it is very sensitive to the tilt angle. This can be seen with respect to the computer simulation of FIG. 4. Here the contours are extended along the x-axis, indicating insensitivity to object position but compressed along the y-axis indicating sensitivity to object tilt.

FIG. 5 is a diagram of a telecentric system 42. Source 44 is an extended source of light. In one preferred embodiment, this source comprises an optical fiber. The source produces an approximately uniform radiance over some range of angles. In a preferred embodiment, the optical fiber provides uniform radiance over the range of about 6 to 7 degrees. The full numerical aperture of the fiber is 0.22. As is discussed later, the stop can be used to allow only this approximate 6 to 7 degrees of uniform radiance to pass through the system. Even though the system will work by using a smaller angle within this uniform radiance cone, it is desired that as much as possible of the approximately uniform radiance cone be used in order to maintain the device's efficiency.

The telecentric illuminating system includes a stop (lens 1) and at least one lens (lens 2), such that the stop is at the front focal point of this at least one lens (lens 2). The telecentric illuminating system 46 then images the source onto the object under measurement 48. The light reflects from the object under measurement 48 into the telecentric receiving system 50. The telecentric receiving system 50 comprises two or more lenses, in this case lens 3 and lens 4. The first lens or a group of lenses, in this case lens 3, forms an image of the stop E (co-located with the lens 1 aperture) at position E'. Position E' is at the front focal point F4 of the final lens or group of lenses, in this case lens 4. Lens 4 relays the image of the source 44 onto the receiver 52, which in a preferred embodiment is an optical fiber.

As shown in FIG. 5, in a preferred embodiment the rear focal point of lens 2 F2' is at the object 48 and the front focal point of lens 3 F3 is also at the object 48.

In the preferred embodiment shown in FIG. 5, the angle, θ, defined between the optical axis 54 and the normal 56 to the object 48 is 11 degrees. A chief ray 58 is shown for the preferred embodiment shown in FIG. 5. Note that it crosses the optical axis 54 at the image E' of the stop. A marginal ray 60 for the system is also illustrated in FIG. 5. The marginal ray crossing the optical axis locates an image plane. Note that there is an image plane at the object 48 and at the detector 52. In this invention, the system will be described as imaging at the detector 52 and object 48 even though the image planes may be slightly off of the object or detector due to the object or detector misposition or tilt. In FIG. 5, the chief ray heights are multiplied by 5 for clarity.

In a preferred embodiment, each of the lenses in the system is used at infinite conjugates. The source is at the front focal point of lens 1 F1. Note that this is not required for the system to work in general, but is a result of the specific lenses chosen to be operated at their designed object/image pair configuration. This is a result of the commercially available lenses, which are usually corrected for infinite conjugates. Lens 2 takes the beam and forms an image of the source at its rear focal point at F2'. This image is at the front focal point of lens 3 F3, so lens 3 also is operating at infinite conjugates. Finally, the last lens takes the pseudo-collimated light and re-images the source at its rear focal point F4'. Since all of the lenses are used at infinite conjugates, the overall magnification is governed by the various effective focal lengths chosen. This is given by the formula $$m_{total} = \frac{f_2 f_4}{f_1 f_3}$$

where $m_{total}$ is the overall magnification and $f_n$ is the effective focal length for lens n.

Note that each of the lenses 1 through 4 could be replaced by multiple lenses which combine to produce the effects of the lenses described. In fact, in the preferred embodiment, each of the lenses shown in FIG. 5 is an achromatic doublet each of which is composed of a positive and negative lens element. An alternate expression for "lens or group of lenses" is "lens arrangement" where the lens arrangement can be a single lens or a group of lens elements.

The optical fiber used for the source and detector is available from C-Technologies, Inc. of Verona, N.J. This optical fiber preferably has a core diameter exceeding 0.05 mm. The telecentric system of FIG. 5 has the benefit that if the object moves parallel to the object normal 56, the system will still be able to produce an accurate reflectance measurement.

As shown in FIG. 14, the detector 52, can be a complex detector including a spectrograph 110 that breaks the received light into its constituent wavelengths. Sub-detectors, such as a charge coupled device (CCD) array 112, can be positioned at locations corresponding to different wavelengths. The relative intensity of the reflections at different wavelengths can give an indication of a coated film thickness. This type of system also is sensitive to object tilt and mis-position and could benefit from the present invention. The complex detector 52' can also use an optical fiber 114 shown in phantom. The spectrograph slit would be preferably overfilled as described above for the simple detector. Alternately, a spectrograph 116 could be used as the source to send different wavelengths of light in different time periods.

FIGS. 6–8 are thin lens diagrams to illuminate the benefits of the present invention. In these diagrams, the 11 degree tilt of the optical axis with respect to the normal to the object is not shown, so that these diagrams will be less cluttered. Looking at FIG. 6, an optical axis 60 is shown. Also shown are chief rays 62 and 64; and marginal rays 66 and 68. In the embodiment shown in FIG. 6, the effective focal lengths in millimeters are shown along a top column. The beam width diameters in millimeters are shown in the middle column and the distances between the optical elements in millimeters are shown in the bottom column. Note that lens 2 has a focal length of 100 millimeters and is positioned 100 millimeters from the stop. Lens 4 has a focal length of 40 millimeters and is positioned 40 millimeters from the virtual stop E'. Note how a uniform "diamond" is produced near the fiber detector. A position 10 millimeters away from the fiber detector is shown to illustrate the path that the light would take if the detector were not there. This gives some indication of the light intensity if the object or the detector were to change in location. Note that in one preferred embodiment, lens 1 is positioned 19 millimeters from the source and has a focal length of 19 millimeters. This means that the light between lenses 1 and 2 is pseudo-collimated.

FIG. 7 shows the optical system shown in FIG. 6, with a 1 degree tilt of the object. This 1 degree tilt changes the path of the light rays after the object. However, the bundle of rays that is intercepted by the detector has essentially the same intensity. A disadvantage of systems which use an afocal relay described above with respect to FIG. 2 is that an object tilt can cause the light rays to miss the detector, thus reducing the apparent reflectance of the object and a consequent loss of accuracy.

FIG. 8 shows an alternate embodiment, which also has two telecentric image spaces but in which none of the lenses are operating at infinite conjugates. It is important to note that the system remains telecentric, since the front focal point of lens 2 is co-located with the stop E (at lens 1) and the front focal point of lens 4 is at the image of the stop E'. The embodiment of FIG. 8 is less preferred because most commercially available lenses are designed to minimize aberrations when operated at infinite conjugates.

FIG. 9 is diagram of a the system of FIG. 5 folded. This system 80 includes a fiber source 82, a pseudo-collimating lens collocated with the stop 84, and a lens 86 for imaging onto an object (not shown). Light from the source 82 passes through the lens and stop 84 to the beam splitter 85. A portion of the light reflects from the beamsplitter 85 then through the lens 86 to form an image of the source 82 on the object (not shown). The optical axis is normal to the object. This increases the tolerance of the system to the object's misposition and any tilt angle deviation from perfectly normal. Light reflected back from the object (not shown) passes through the lens 86 and beam splitter 85 to lens 88. This lens re-images the source 82 on the detector 90.

The telecentric illuminating system comprises the lens 84 and lens 86 and beamsplitter 85. The telecentric receiving system comprises lenses 86 and 88 and beamsplitter 85. The illumination system is telecentric, which means that the stop (lens 84) is at the front focal point of lens 86 for light traveling from the source 82 through lens 84, reflecting from the beamsplitter 85, and traveling to lens 86. The lens 88 has a focal point at the image of the stop formed between lens 86 and lens 88. In this system, the lenses are preferably operated at infinite conjugates, so that the marginal ray is parallel to the axis between lens 84 and 86 and between lens 88 and 86. This places the beam splitter in a space of nearly parallel light rays. Placing the beam splitter in this space minimizes the range of angles of incidence seen by the beam splitter and thus the performance of the beam splitter is closer to the ideal. See H. A. Macleod's book, *Thin Film Optical Filters* (2d ed., Macmillan, 1986, pp. 462–473) for a thorough discussion of the effects of an interference filter placement in optical systems. A disadvantage of the system of FIG. 9 is that only part of the light that comes from source 82 is reflected by the beam splitter 85 to the object and only part of the light reflected by the object is transmitted through beam splitter 85 and relayed onto the detector 90. This means that the overall efficiency of the device is reduced by at least seventy-five percent.

FIG. 10 is a computer simulation showing the throughput for the telecentric system with the 11 degree incidence angle similar to that shown in FIG. 5. The object position shown along the x-axis and the object tilt angle is shown along the y-axis. This simulation shows a large central area 92 for which the throughput and thus the resultant reflectance measurements are essentially constant. The specific throughput value is not crucial since the system can be calibrated. What is important is that the throughput, thus the reflectance measurements, remain essentially constant with small changes in object position and tilt. The result shown in FIG. 10 is especially good compared to the focal system and the afocal collimating system of FIGS. 3 and 4, respectively.

FIG. 11 is the computer simulation for the folded telecentric system similar to FIG. 9. The throughput remains essentially constant for a very large area of the graph. Note that regions 94 and 96 have a close system throughput and may be the same but an artifact of the choice of the distribution, weights and number of rays used in the simulation makes them appear different.

FIG. 12 shows real data for a prototype folded telecentric system similar to FIG. 9. There is an essentially stable region 98 centered about 0 degrees part tilt and 70.2 mm objective to part distance.

FIG. 13 shows a telecentric system 100. The telecentric system includes a lens which is co-located with the system stop 102 and a second lens 104. Lens 104 has its front focal point at the aperture stop 102, so that the system is telecentric. A object to be measured is also the light source 106. A detector is positioned at 108. This system gives the advantage that a defocus of the object 106 or the poorly positioned detector 108 results in a minimal change in the irradiance measured at detector 108. The system could also be used to measure the radiant intensity or radiance of a source.

Although several preferred embodiments of this invention have been described in detail herein with reference to the accompanying drawings, it is to be understood that the invention is not limited to these precise embodiments, and that various changes and modifications may be effected therein by one skilled in the art without departing from the scope or spirit of the invention as described in the appended claims.

What is claimed is:

1. An optical system for measuring the reflectance of an object comprising:

a source of light with approximately uniform radiance over a range of angles;

a telecentric illuminating system comprising an aperture stop chosen such that ray angles passed by the stop are within the range where the source is approximately uniform in radiance; and one or more lenses used to image the source onto the object to be measured; and a telecentric receiving system arranged to collect the light spectrally reflected from the object, the telecentric receiving system comprising two or more lenses and positioned relative to the object and illuminating system such that an image of the stop of the illuminating system is formed in such a manner as to make the receiving system telecentric, and such that the image of the source reflected from the object and re-imaged on the detector is relayed such that the image of the source at the detector is larger than the detector.

2. The optical system of claim 1, wherein one of the lenses of the telecentric illuminating system acts as the aperture stop of the system.

3. The optical system of claim 2, wherein the lens that acts as the aperture stop is operating at infinite conjugates.

4. The optical system of claim 1, wherein the source comprises an optical fiber relaying light from a remote light source.

5. The optical system of claim 1, wherein the detector comprises a fiber-optic relay to a remote detector.

6. The optical system of claim 1, wherein the source is comprised of light source whose light goes through a spectrograph.

7. The optical system of claim 1, wherein the detector is comprised of a spectrograph and detector.

8. The optical system of claim 1, wherein the source comprises an optical fiber relaying light from a remote light source that has passed through a spectrograph.

9. The optical system of claim 1, wherein the detector comprises a fiber-optic relay to a remote spectrograph and detector.

10. The optical system of claim 1, wherein the telecentric illuminating system and telecentric receiving system include a beamsplitter such that at least one lens is common to both the illuminating system and receiving system.

11. The optical system of claim 1, wherein the receiving system is allowed to deviate from the ideal position relative to the object without affecting the system throughput.

12. The optical system of claim 1, wherein the illuminating system is allowed to deviate from the ideal position relative to the object without affecting the system throughput.

13. The optical system of claim 1, wherein the illuminating system and receiving systems are allowed to deviate from their ideal positions relative to the object without affecting the system throughput.

14. A method of measuring the reflectance of an object comprising the steps of:

producing a source of light with approximately uniform radiance over a range of angles;

passing the light through a telecentric illuminating system comprising an aperture stop and one or more lenses so as to image the source onto the object under measurement;

reflecting light from the object;

collecting the reflected light through a telecentric receiving system, comprising two or more lenses, positioned relative to the object and illumination system such that an image of the stop of the illuminating system is formed in such a manner as to make the receiving system telecentric, and relaying the image of the source reflected from the object and re-imaging it on a detector such that the image of the source at the detector is larger than the detector.

15. The reflectance measuring method of claim 14, wherein the receiving system is allowed to deviate from the ideal position relative to the object without affecting the system throughput.

16. The reflectance measuring method of claim 14, wherein the illuminating system is allowed to deviate from the ideal position relative to the object without affecting the system throughput.

17. The reflectance measuring method of claim 14, wherein the illuminating system and receiving systems are allowed to deviate from their ideal positions relative to the object without affecting the system throughput.

* * * * *